(12) United States Patent
Yokoyama et al.

(10) Patent No.: US 11,945,318 B2
(45) Date of Patent: Apr. 2, 2024

(54) POWER SUPPLY APPARATUS AND POWER SUPPLY METHOD

(71) Applicant: TOYOTA JIDOSHA KABUSHIKI KAISHA, Aichi-ken (JP)

(72) Inventors: Daiki Yokoyama, Gotemba (JP); Toshiya Hashimoto, Miyoshi (JP); Shuntaro Okazaki, Shizuoka-ken (JP); Shogo Tsuge, Fuji (JP); Kazuhisa Matsuda, Shizuoka-ken (JP)

(73) Assignee: TOYOTA JIDOSHA KABUSHIKI KAISHA, Aichi-ken (JP)

( * ) Notice: Subject to any disclaimer, the term of this patent is extended or adjusted under 35 U.S.C. 154(b) by 0 days.

(21) Appl. No.: 17/844,723

(22) Filed: Jun. 21, 2022

(65) Prior Publication Data

US 2022/0410731 A1   Dec. 29, 2022

(30) Foreign Application Priority Data

Jun. 23, 2021 (JP) ................. 2021-104238

(51) Int. Cl.
| | |
|---|---|
| *B60L 53/12* | (2019.01) |
| *A61N 1/37* | (2006.01) |
| *B60L 53/60* | (2019.01) |
| *H02J 50/12* | (2016.01) |
| *H02J 50/40* | (2016.01) |
| *H02J 50/60* | (2016.01) |

(52) U.S. Cl.
CPC ............. *B60L 53/12* (2019.02); *A61N 1/37* (2013.01); *B60L 53/60* (2019.02); *H02J 50/12* (2016.02); *H02J 50/40* (2016.02); *H02J 50/60* (2016.02)

(58) Field of Classification Search
CPC ........ B60L 53/12; B60L 53/122; H02J 50/12; H02J 50/40; Y02T 10/7072; Y02T 90/14
See application file for complete search history.

(56) References Cited

U.S. PATENT DOCUMENTS

| | | | |
|---|---|---|---|
| 2012/0217111 A1* | 8/2012 | Boys ...................... | H01F 38/14 191/10 |
| 2014/0097671 A1 | 4/2014 | Nakamura et al. | |
| 2020/0156488 A1* | 5/2020 | Tsukamoto ........ | G07C 9/00182 |
| 2022/0266004 A1* | 8/2022 | Catanzaro ............... | A61N 1/08 |

FOREIGN PATENT DOCUMENTS

| | | |
|---|---|---|
| JP | 2018157686 A | 10/2018 |
| JP | 201913100 A | 1/2019 |
| WO | 2012176264 A1 | 12/2012 |

* cited by examiner

*Primary Examiner* — Daniel Kessie
*Assistant Examiner* — Terrence R Willoughby
(74) *Attorney, Agent, or Firm* — HAUPTMAN HAM, LLP (57) ABSTRACT

The power supply apparatus includes a power transmission apparatus configured to transmit power to a power reception apparatus of the vehicle by non-contact and a processor configured to control the power transmission apparatus, detect a pickup/dropoff operation at the vehicle when power is being supplied by non-contact from the power supply apparatus to the vehicle, and detect a number of surrounding vehicles being supplied with power by non-contact in a predetermined range at surroundings of the power supply apparatus. The processor is configured to decrease power transmitted from the power transmission apparatus to the power reception apparatus when detecting a pickup/dropoff operation, and determine an amount of decrease of the transmitted power based on the number of surrounding vehicles.

11 Claims, 9 Drawing Sheets

POWER SUPPLY APPARATUS AND POWER SUPPLY METHOD

RELATED APPLICATIONS

The present application claims priority of Japanese Patent Application No. 2021-104238 filed Jun. 23, 2021, the disclosure of which is hereby incorporated by reference herein in its entirety.

FIELD

The present disclosure relates to a power supply apparatus and a power supply method.

BACKGROUND

PTL 1 discloses supplying power wirelessly to wearable equipment in a manner so that the human body wearing that wearable equipment is not unnecessarily biologically acted upon by electromagnetic waves.

Further, it has been known in the past to transmit power by non-contact to vehicles from a power supply apparatus provided at a ground surface. In regard to this, PTL 2 discloses avoiding any detrimental effect on equipment etc. owned by passengers by lowering the power transmitted to a vehicle from a power supply apparatus if it is detected that a door of the vehicle is opened.

CITATION LIST

Patent Literature

[PTL 1] Japanese Unexamined Patent Publication No. 2019-013100
[PTL 2] WO2012/176264

SUMMARY

Technical Problem

However, PTL 2 does not consider at all the effect of electromagnetic waves emitted from other power supply apparatuses for supplying power to surrounding vehicles at the surroundings of a vehicle when supplying power by non-contact to the vehicle from a power supply apparatus. For this reason, even if lowering the power transmitted to a vehicle from a power supply apparatus, the effect of reducing the electromagnetic waves is liable to be insufficient.

Therefore, in consideration of the above problem, an object of the present disclosure is to consider also electromagnetic waves generated for supplying power to surrounding vehicles and reduce the effect of electromagnetic waves on electronic equipment etc. of passengers of a vehicle if there is a pickup or dropoff at the vehicle when power is supplied by non-contact to the vehicle from a power supply apparatus.

Solution to Problem

The summary of the present disclosure is as follows.

(1) A power supply apparatus for supplying power to a vehicle by non-contact, comprising: a power transmission apparatus configured to transmit power to a power reception apparatus of the vehicle by non-contact; and a processor configured to control the power transmission apparatus, detect a pickup/dropoff operation at the vehicle when power is being supplied by non-contact from the power supply apparatus to the vehicle, and detect a number of surrounding vehicles being supplied with power by non-contact in a predetermined range at surroundings of the power supply apparatus, wherein the processor is configured to decrease power transmitted from the power transmission apparatus to the power reception apparatus when detecting a pickup/dropoff operation, and determine an amount of decrease of the transmitted power based on the number of surrounding vehicles.

(2) The power supply apparatus described in above (1), wherein the processor is configured to stop power transmission from the power transmission apparatus to the power reception apparatus if a passenger being picked up or dropped off is wearing a pacemaker when detecting a pickup/dropoff operation.

(3) The power supply apparatus described in above (1) or (2), wherein the processor is configured to identify the number of passengers being picked up or dropped off, and determine the amount of decrease of the transmitted power based on the number of surrounding vehicles and the number of passengers.

(4) A power supply method including: transmitting power from a power transmission apparatus of a power supply apparatus to a power reception apparatus of a vehicle by non-contact to supply power from the power supply apparatus to the vehicle by non-contact; detecting a pickup/dropoff operation at the vehicle when power is being supplied from the power supply apparatus to the vehicle by non-contact; detecting a number of surrounding vehicles being supplied with power by non-contact in a predetermined range at the surroundings of the power supply apparatus; and decreasing the power transmitted from the power transmission apparatus to the power reception apparatus when a pickup/dropoff operation is detected and determining an amount of decrease of the transmitted power based on the number of surrounding vehicles.

According to the present disclosure, it is possible to more effectively reduce the effect of electromagnetic waves on electronic equipment etc. of passengers of a vehicle if there is a pickup or dropoff at the vehicle when power is supplied by non-contact to the vehicle from a power supply apparatus.

DESCRIPTION OF EMBODIMENTS

Below, referring to the drawings, embodiments of the present disclosure will be explained in detail. Note that, in the following explanation, similar component elements will be assigned the same reference notations.

First Embodiment

Below, referring to FIG. 1 to FIG. 6, a first embodiment of the present disclosure will be explained.

Figure 1:
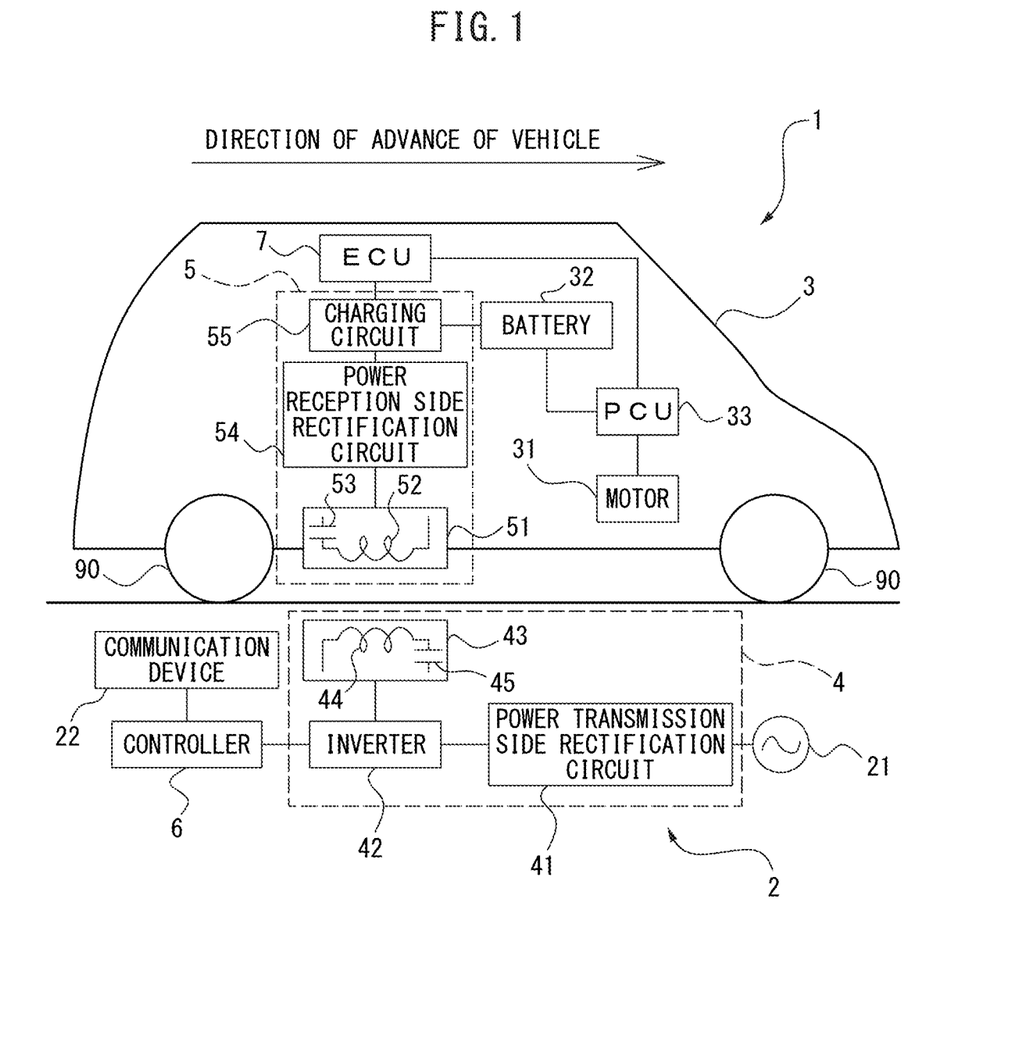
FIG. 1 is a view schematically showing a configuration of a non-contact power supply system according to a first embodiment of the present disclosure.

FIG. 1 is a view schematically showing a configuration of a non-contact power supply system 1 according to the first embodiment of the present disclosure. The non-contact power supply system 1 is provided with a power supply apparatus 2 and a vehicle 3 and supplies power by non-contact between the power supply apparatus 2 and the vehicle 3. In particular, in the present embodiment, the non-contact power supply system 1 transmits power by non-contact from the power supply apparatus 2 to the vehicle 3 by magnetic field resonance coupling (magnetic field resonance) when the vehicle 3 is running. That is, the non-contact power supply system 1 transmits power from the power supply apparatus 2 to the vehicle 3 using a magnetic field as a medium. Note that, non-contact power supply is also called non-contact power transfer, wireless power transfer, or wireless power supply.

The power supply apparatus 2 supplies power to the vehicle 3 by non-contact. As shown in FIG. 1, the power supply apparatus 2 is provided with a power transmission apparatus 4, a power supply 21, a controller 6, and a communication device 22. In the present embodiment, the power supply apparatus 2 is provided at a road (lane) on which the vehicle 3 runs and, for example, is buried in the ground (under the road surface). Note that, at least a part of the power supply apparatus 2 (for example, the power supply 21, the controller 6, and the communication device 22) may be placed on the road surface.

The power supply 21 is the power source of the power transmission apparatus 4 and supplies power to the power transmission apparatus 4. The power supply 21, for example, is a commercial alternating current power supply supplying single-phase alternating current power. Note that, the power supply 21 may be an alternating current power supply supplying three-phase alternating current power etc.

The power transmission apparatus 4 is configured to transmit power by non-contact to a power reception apparatus 5 of the vehicle 3 described later. In the present embodiment, the power transmission apparatus 4 is provided with a power transmission side rectification circuit 41, an inverter 42, and a power transmission side resonance circuit 43. In the power transmission apparatus 4, suitable alternating current power (high frequency power) is supplied through the power transmission side rectification circuit 41 and the inverter 42 to the power transmission side resonance circuit 43.

The power transmission side rectification circuit 41 is electrically connected to the power supply 21 and the inverter 42. The power transmission side rectification circuit 41 rectifies the alternating current power supplied from the power supply 21 to direct current power and supplies the direct current power to the inverter 42. The power transmission side rectification circuit 41 is, for example, an AC/DC converter.

The inverter 42 is electrically connected to the power transmission side rectification circuit 41 and power transmission side resonance circuit 43. The inverter 42 converts the direct current power supplied from the power transmission side rectification circuit 41 to alternating current power of a frequency higher than the alternating current power of the power supply 21 (high frequency power) and supplies the high frequency power to the power transmission side resonance circuit 43.

The power transmission side resonance circuit 43 has a resonator comprised of a coil 44 and capacitor 45. The various parameters of the coil 44 and capacitor 45 (outside diameter and inside diameter of the coil 44, turns of the coil 44, electrostatic capacity of the capacitor 45, etc.) are determined so that the resonance frequency of the power transmission side resonance circuit 43 becomes a predetermined set value. The predetermined set value is, for example, 10 kHz to 100 GHz, preferably is the 85 kHz determined by the SAE TIR J2954 standard as the frequency band for non-contact power supply of vehicles.

The power transmission side resonance circuit 43 is arranged at the center of the lane over which the vehicle 3 runs so that the center of the coil 44 is positioned at the center of the lane. If high frequency power supplied from the inverter 42 is applied to the power transmission side resonance circuit 43, the power transmission side resonance circuit 43 generates an alternating current magnetic field for transmitting the power to the vehicle 3. Note that, the power supply 21 may be a fuel cell or solar cell or other such direct current power supply. In this case, the power transmission side rectification circuit 41 may be omitted.

The controller 6 is, for example, a general use computer and performs various control of the power supply apparatus 2. For example, the controller 6 is electrically connected to the inverter 42 of the power transmission apparatus 4 and controls the inverter 42 so as to control the power transmission by the power transmission apparatus 4.

Figure 2:
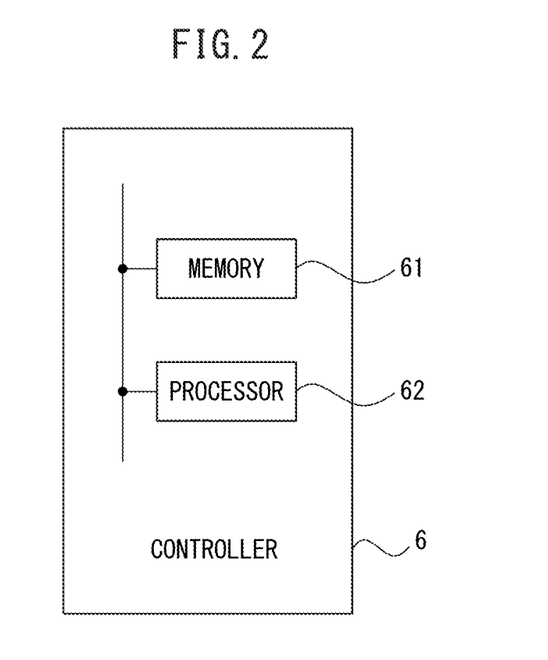
FIG. 2 is a schematic view of a configuration of a controller of a power supply apparatus.

FIG. 2 is a schematic view of the configuration of the controller 6. The controller 6 is provided with a memory 61 and a processor 62. The memory 61 and the processor 62 are connected with each other through signal wires. Note that, the controller 6 may be further provided with a communication interface etc. for connecting the controller 6 to a communication network such as the Internet.

The memory 61 has, for example, a volatile semiconductor memory (for example, a RAM) and a nonvolatile semiconductor memory (for example, a ROM). The memory 61 stores programs to be run at the processor 62, various data used when various processing is performed by the processor 62, etc.

The processor 62 has one or more CPUs (central processing units) and their peripheral circuits and performs various processing. Note that, the processor 62 may also have a logic unit or arithmetic unit or other such processing circuit. The processor 62 is one example of a control part of the power supply apparatus 2.

The communication device 22 is equipment enabling communication between the power supply apparatus 2 and the outside of the power supply apparatus 2 (for example, a near field wireless communication module). The communication device 22 is electrically connected to the controller 6. The controller 6 communicates with the vehicle 3 through the communication device 22.

On the other hand, the vehicle 3 is supplied with power by non-contact by the power supply apparatus 2 when passing over the power transmission side resonance circuit 43 of the power supply apparatus 2. As shown in FIG. 1, the vehicle 3 is provided with a power reception apparatus 5, a motor 31, a battery 32, a power control unit (PCU) 33, and an electronic control unit (ECU) 7. In the present embodiment, the vehicle 3 is an electric vehicle (EV) not mounting an internal combustion engine, and the motor 31 outputs drive power for running use.

The motor 31 is, for example, an alternating current synchronous motor and functions as a motor and a generator. When the motor 31 functions as a motor, the power stored in the battery 32 is used as the source of power for driving it. The output of the motor 31 is transmitted through a decelerator and axle to the wheels 90. On the other hand, at the time of deceleration of the vehicle 3, the motor 31 is driven by rotation of the wheels 90 and the motor 31 functions as a generator to produce regenerated power.

The battery 32 is a rechargeable secondary battery and is, for example, comprised of a lithium ion battery, nickel-hydrogen battery, etc. The battery 32 stores the power required for the vehicle 3 to run (for example, drive power of motor 31). If the regenerated power produced by the motor 31 is supplied to the battery 32, the battery 32 is charged and the state of charge of the battery 32 is restored. Further, the battery 32 can be charged by an outside power supply other than the power supply apparatus 2 through a charging port provided at the vehicle 3.

The PCU 33 is electrically connected to the battery 32 and motor 31. The PCU 33 has an inverter, booster converter, and DC/DC converter. The inverter converts the direct current power supplied from the battery 32 to alternating current power and supplies the alternating current power to the motor 31. On the other hand, the inverter converts the alternating current power generated by the motor 31 (regenerated power) to direct current power and supplies the direct current power to the battery 32. When the power stored in the battery 32 is supplied to the motor 31, the booster converter boosts the voltage of the battery 32 in accordance with need. When the power stored in the battery 32 is supplied to the headlights and other electronic equipment, the DC/DC converter lowers the voltage of the battery 32.

The power reception apparatus 5 is configured to receive power by non-contact from the power transmission apparatus 4. In the present embodiment, the power reception apparatus 5 is provided with a power reception side resonance circuit 51, power reception side rectification circuit 54, and charging circuit 55. The power reception apparatus 5 receives power from the power transmission apparatus 4 and supplies the received power to the battery 32.

The power reception side resonance circuit 51 is arranged at the bottom part of the vehicle 3 so that the distance from the road surface becomes smaller. In the present embodiment, the power reception side resonance circuit 51 is arranged at the center of the vehicle 3 in the vehicle width direction and is arranged between the front wheels 90 and the rear wheels 90 in the front-back direction of the vehicle 3.

The power reception side resonance circuit 51 has a configuration similar to the power transmission side resonance circuit 43 and has a resonator comprised of a coil 52 and capacitor 53. The various parameters of the coil 52 and capacitor 53 (outside diameter and inside diameter of the coil 52, turns of the coil 52, electrostatic capacity of the capacitor 53, etc.) are determined so that the resonance frequency of the power reception side resonance circuit 51 matches the resonance frequency of the power transmission side resonance circuit 43. Note that, if the amount of deviation of the resonance frequency of the power reception side resonance circuit 51 and the resonance frequency of the power transmission side resonance circuit 43 is small, for example, the resonance frequency of the power reception side resonance circuit 51 is within a range of ±20% of the resonance frequency of the power transmission side resonance circuit 43, the resonance frequency of the power reception side resonance circuit 51 does not necessarily have to match the resonance frequency of the power transmission side resonance circuit 43.

As shown in FIG. 1, when the power reception side resonance circuit 51 faces the power transmission side resonance circuit 43, if an alternating current magnetic field is generated at the power transmission side resonance circuit 43, the vibration of the alternating current magnetic field is transferred to the power reception side resonance circuit 51 which resonates by the same resonance frequency of the power transmission side resonance circuit 43. As a result, due to electromagnetic induction, an induction current flows to the power reception side resonance circuit 51, and due to the induction current, power is generated at the power reception side resonance circuit 51. That is, the power transmission side resonance circuit 43 transmits power to the power reception side resonance circuit 51 through a magnetic field, and the power reception side resonance circuit 51 receives power from the power transmission side resonance circuit 43 through a magnetic field.

The power reception side rectification circuit 54 is electrically connected to the power reception side resonance circuit 51 and the charging circuit 55. The power reception side rectification circuit 54 rectifies the alternating current power supplied from the power reception side resonance circuit 51 to convert it to direct current power and supplies the direct current power to the charging circuit 55. The power reception side rectification circuit 54 is, for example, an AC/DC converter.

The charging circuit 55 is electrically connected to the power reception side rectification circuit 54 and the battery 32. The charging circuit 55 converts the direct current power supplied from the power reception side rectification circuit 54 to the voltage level of the battery 32 and supplies it to the battery 32. If the power transmitted from the power transmission apparatus 4 is supplied by the power reception apparatus 5 to the battery 32, the battery 32 is charged and the SOC of the battery 32 is restored. The charging circuit 55 is, for example, a DC/DC converter.

The ECU 7 performs various types of control of the vehicle 3. For example, the ECU 7 is electrically connected to the charging circuit 55 of the power reception apparatus 5 and controls the charging circuit 55 to control charging of the battery 32 by the power transmitted from the power transmission apparatus 4. Further, the ECU 7 is electrically connected to the PCU 33 and controls the PCU 33 to control the transmission of power between the battery 32 and vehicle-mounted equipment (for example, the motor 31). Note that, the ECU 7 may supply the power received from the power transmission apparatus 4 through the power reception apparatus 5 to an electrical load (for example, the motor 31) instead of the battery 32.

Figure 3:
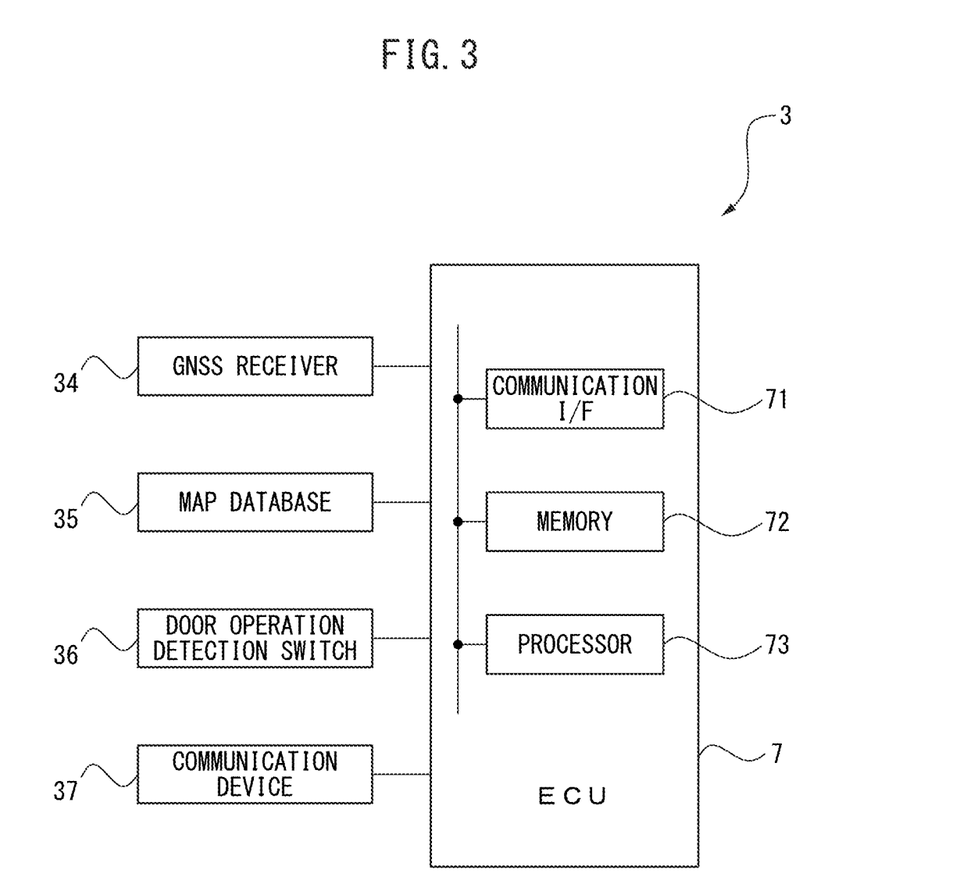
FIG. 3 is a view showing a schematic configuration of an ECU of a vehicle and other vehicle-mounted equipment.

FIG. 3 is a view showing a schematic configuration of the ECU 7 and other vehicle-mounted equipment. The ECU 7 has a communication interface 71, a memory 72, and a processor 73. The communication interface 71, the memory 72, and the processor 73 are connected together through signal wires.

The communication interface 71 has an interface circuit for connecting the ECU 7 to an internal vehicle network based on the CAN (Controller Area Network) or other standard.

The memory 72, for example, has a volatile semiconductor memory (for example, RAM) and nonvolatile semiconductor memory (for example, ROM). The memory 72 stores programs to be run at the processor 73, various data used when various processing is performed by the processor 73, etc.

The processor 73 has one or more CPUs (central processing units) and their peripheral circuits and performs various processing. Note that, the processor 73 may also have a logic unit or arithmetic unit or other such processing circuit.

Further, as shown in FIG. 3, the vehicle 3 is further provided with a GNSS receiver 34, a map database 35, a door operation detection switch 36 and a communication device 37. The GNSS receiver 34, the map database 35, the door operation detection switch 36 and the communication device 37 are electrically connected to the ECU 7.

The GNSS receiver 34 detects the current position of the vehicle 3 (for example, a latitude and longitude of the vehicle 3) based on position measurement information obtained from a plurality of (for example, three or more) positioning satellites. Specifically, the GNSS receiver 34 captures a plurality of positioning satellites and receives signals emitted from the positioning satellites. Further, the GNSS receiver 34 calculates the distances to the positioning satellites based on the difference between the times of emission and times of reception of the signals and detects the current position of the vehicle 3 based on the distances to the positioning satellites and the positions of the positioning satellites (orbital information). The output of the GNSS receiver 34, that is, the current position of the vehicle 3 detected by the GNSS receiver 34, is sent to the ECU 7.

Note that, "GNSS" (Global Navigation Satellite System) is a general name of the GPS of the U.S., GLONASS of Russia, Galileo of Europe, QZSS of Japan, BeiDou of China, IRNSS of India, and other satellite positioning systems. Therefore, the GNSS receiver 34 includes a GPS receiver.

The map database 35 stores map information. The map information includes position information of the power supply apparatuses 2, etc. The ECU 7 acquires map information from the map database 35. Note that, the map database 35 may be provided outside of the vehicle 3 (for example, the server etc.), and the ECU 7 may acquire map information from outside the vehicle 3.

A door operation detection switch 36 detects operation (opening and closing) of a door of the vehicle 3. The output of the door operation detection switch 3 is transmitted to the ECU 7. The door operation detection switch 36, for example, is a courtesy switch which turns on/off linked with operation of a door of the vehicle 3.

The communication device 37 is equipment enabling communication between the vehicle 3 and the outside of the vehicle 3 (for example, near field wireless communication module, a data communication module (DCM) for connecting the vehicle 3 to a communication network such as the Internet, etc.) The ECU 7 communicates with the power supply apparatus 2 through the communication device 37.

For example, ECU 7 emits a power supply request signal requesting power supply to the vehicle 3 from the power supply apparatus 2 using the communication device 37 when the vehicle 3 approaches a power supply area in which the power transmission apparatus 4 of the power supply apparatus 2 is installed. If receiving a power supply request signal from the vehicle 3, the controller 6 of the power supply apparatus 2 generates an alternating magnetic field for power transmission use by the power transmission apparatus 4. That is, if receiving a power supply request signal from the vehicle 3, the controller 6 starts to supply power by non-contact to the vehicle 3 from the power supply apparatus 2.

If power is supplied by non-contact to the vehicle 3 from the power supply apparatus 2, electromagnetic waves will be generated at the surroundings of the vehicle 3 by the alternating magnetic field generated from the power transmission side resonance circuit 43 of the power transmission apparatus 4. Even if such electromagnetic waves are generated, the electromagnetic waves can be prevented from entering the passenger compartment by an electromagnetic shield etc. provided at the vehicle 3. For this reason, when power is transmitted from the power transmission apparatus 4 of the power supply apparatus 2 to the power reception apparatus 5 of the vehicle 3, the electromagnetic waves accompanying power transmission will not affect electronic equipment etc. of passengers inside the passenger compartment.

However, if there is a pickup at the vehicle 3 or dropoff from the vehicle 3 when the vehicle 3 is temporarily stopped, the passenger will be near the vehicle 3 at the outside of the vehicle 3. If power is supplied to the vehicle 3 in this state, the degree of the effect of electromagnetic waves on electronic equipment etc. of the passenger of the vehicle 3 will become greater. For this reason, in the present embodiment, while the vehicle 3 is being supplied with power, it will be monitored for pickup/dropoff. If a pickup/dropoff operation is detected, the power transmitted from the power transmission apparatus 4 to the power reception apparatus 5 will be decreased. By doing this, the effect of electromagnetic waves on electronic equipment etc. of a passenger of the vehicle 3 can be reduced.

However, if a surrounding vehicle is being supplied with power by non-contact at the surroundings of the vehicle 3 at which pickup or dropoff occurs, a passenger of the vehicle 3 is liable to be affected by the electromagnetic waves generated from another power supply apparatus different from the power supply apparatus 2 supplying power by non-contact to the vehicle 3. For this reason, in the present embodiment, when a pickup/dropoff operation at the vehicle 3 is detected, the state of power supply at the surroundings is considered to determine the amount of decrease in the power transmitted from the power transmission apparatus 4 to the power reception apparatus 5. By doing this, even if there is a pickup or dropoff at a vehicle 3 when power is being supplied by non-contact from the power supply apparatus 2 to the vehicle 3, it is possible to more effectively reduce the effect of electromagnetic waves on the passenger of the vehicle 3.

Figure 4:
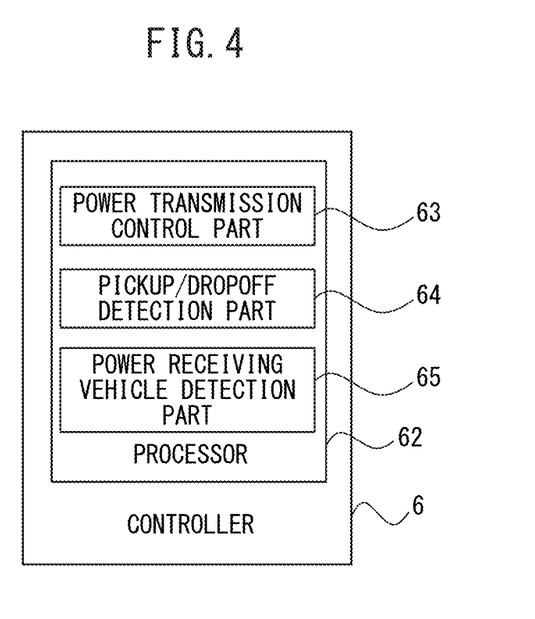
FIG. 4 is a functional block diagram of a processor of a controller.

The above-mentioned control is performed by the controller 6 of the power supply apparatus 2. FIG. 4 is a functional block diagram of a processor 62 of the controller 6. In the present embodiment, the processor 62 is provided with a power transmission control part 63, a pickup/dropoff detection part 64 and a power receiving vehicle detection part 65. The power transmission control part 63, the pickup/dropoff detection part 64 and the power receiving vehicle detection part 65 are functional modules realized by a computer program stored in a memory 61 of the controller 6 being run by the processor 62 of the controller 6. Note that, the power transmission control part 63, the pickup/dropoff detection part 64, and the power receiving vehicle detection part 65 may be realized by dedicated processing circuits provided at the processor 62.

The power transmission control part 63 controls the power transmission apparatus 4. For example, the power transmission control part 63 controls the inverter 42 of the power transmission apparatus 4 to control the power transmitted from the power transmission apparatus 4 to the power reception apparatus 5. Note that, the "power transmitted from the power transmission apparatus 4 to the power reception apparatus 5" means the amount of power per unit time transmitted from the power transmission apparatus 4 to the power reception apparatus 5.

The pickup/dropoff detection part 64 detects a pickup/dropoff operation at the vehicle 3 when power is being supplied by non-contact from the power supply apparatus 2 to the vehicle 3. In other words, the pickup/dropoff detection part 64 detects a pickup at the vehicle 3 and a dropoff from the vehicle 3 when power is being transmitted from the power transmission apparatus 4 to the power reception apparatus 5. The power receiving vehicle detection part 65 detects the number of surrounding vehicles being supplied with power by non-contact in a predetermined range at the surroundings of the power supply apparatus 2 (below, referred to as "the number of power receiving vehicles").

When a pickup/dropoff operation is detected by the pickup/dropoff detection part 64, the power transmission control part 63 decreases the power transmitted from the power transmission apparatus 4 to the power reception apparatus 5, and determines the amount of decrease in the transmitted power based on the number of the power receiving vehicles detected by the power receiving vehicle detection part 65.

Figure 5:
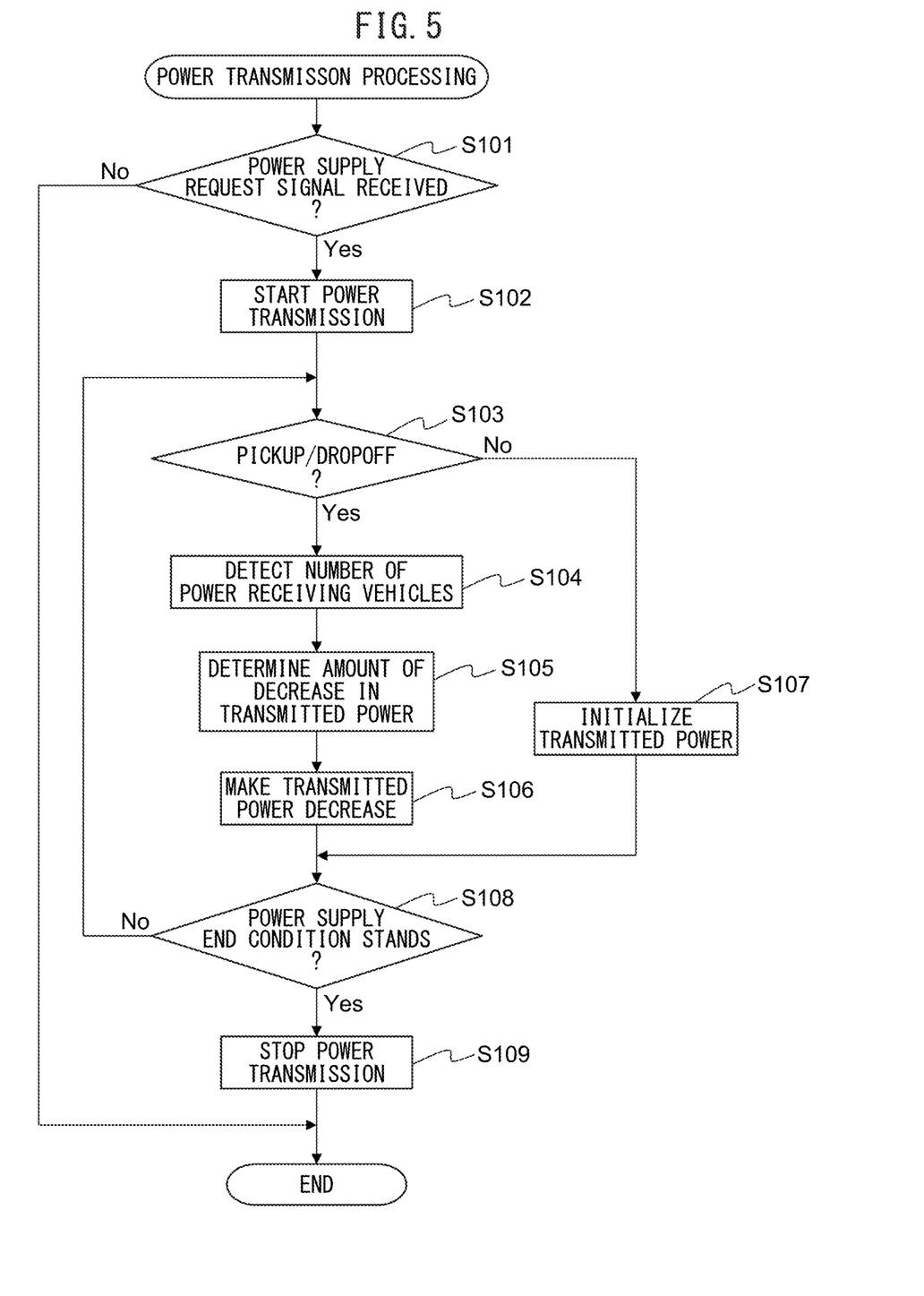
FIG. 5 is a flow chart showing a control routine of power transmission processing in the first embodiment of the present disclosure.

Below, referring to the flow chart of FIG. 5, the flow of the above-mentioned control will be explained. FIG. 5 is a flow chart showing a control routine of power transmission processing in the first embodiment of the present disclosure. The present control routine is repeatedly performed by the controller 6 of the power supply apparatus 2.

First, at step S101 the power transmission control part 63 judges whether it has received a power supply request signal from the vehicle 3. If it is judged that it has not received a power supply request signal, the present control routine ends. On the other hand, if it is judged that it has received a power supply request signal, the present control routine proceeds to step S102.

At step S102, the power transmission control part 63 starts to transmit power from the power transmission apparatus 4 to the power reception apparatus 5. Specifically, the power transmission control part 63 supplies alternating current power to the power transmission side resonance circuit 43 by the inverter 42. As a result, an alternating magnetic field is generated from the power transmission side resonance circuit 43, and power is supplied through the alternating magnetic field from the power transmission apparatus 4 to the power reception apparatus 5. That is, non-contact power supply from the power supply apparatus 2 to the vehicle 3 is started.

Next, at step S103 the pickup/dropoff detection part 64 judges whether there is a pickup/dropoff operation at the vehicle 3. For example, a pickup/dropoff operation is detected at the vehicle 3 side, and the result of detection of a pickup/dropoff operation is transmitted from the vehicle 3 to the power supply apparatus 2 through the communication device 37 of the vehicle 3 and the communication device 22 of the power supply apparatus 2. That is, the pickup/dropoff detection part 64 judges whether there is a pickup/dropoff operation at the vehicle 3 based on the result of detection of a pickup/dropoff operation at the vehicle 3. In this case, for example, if a door of the vehicle 3 being opened is detected by the door operation detection switch 36, the ECU 7 of the vehicle 3 detects a pickup/dropoff operation at the vehicle 3 and transmits the result of detection of a pickup/dropoff operation to the power supply apparatus 2.

Note that, the ECU 7 may detect a pickup/dropoff operation at the vehicle 3 using another detection device instead of the door operation detection switch 36 or in addition to the door operation detection switch 36. Examples of other detection devices include an internal vehicle camera generating an image of the inside of a passenger compartment, seat belt sensors detecting fastening of seatbelts, seating sensors detecting seating of passengers, a weight sensor detecting a weight of the vehicle 3, etc. Further, a detection device like a camera or human presence sensor may be provided at the power supply apparatus 2, and the pickup/dropoff detection part 64 may use the detection device provided at the power supply apparatus 2 to judge whether there is a pickup/dropoff operation at the vehicle 3.

If at step S103 it is judged that there is a pickup/dropoff operation, the present control routine proceeds to step S104. At step S104, the power receiving vehicle detection part 65 detects the number of the power receiving vehicles. For example, if a plurality of power transmission apparatuses arranged separated from each other on the road in the direction of advance of a vehicle 3 is controlled by a single controller 6, the power receiving vehicle detection part 65 detects the number of the power receiving vehicles based on the state of power transmission of the power transmission apparatuses other than the power transmission apparatus 4 transmitting power to the power reception apparatus 5 of the vehicle 3 at which a pickup/dropoff operation is detected. Note that, the power receiving vehicle detection part 65 may detect the number of the power receiving vehicles based on power supply information transmitted to the power supply apparatus 2 from vehicles other than the vehicle 3 at which a pickup/dropoff operation is detected or from a server at the outside of the power supply apparatus 2.

Figure 6:
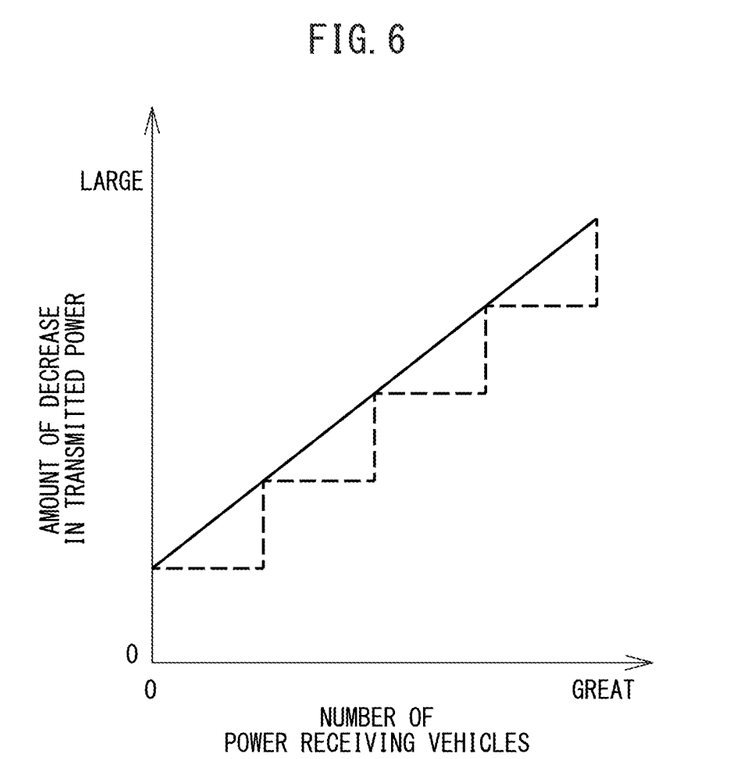
FIG. 6 is a view showing one example of a relationship between a number of power receiving vehicles and an amount of decrease in transmitted power.

Next, at step S105, the power transmission control part 63 determines the amount of decrease in the power transmitted from the power transmission apparatus 4 to the power reception apparatus 5 based on the number of the power receiving vehicles detected by the power receiving vehicle detection part 65. Specifically, the power transmission control part 63 increases the amount of decrease in the transmitted power if the number of the power receiving vehicles is equal to or greater than a predetermined value compared to if the number of the power receiving vehicles is less than the predetermined value. FIG. 6 is a view showing one example of the relationship between the number of the power receiving vehicles and the amount of decrease in the transmitted power. As shown in FIG. 6, the amount of decrease in the transmitted power is made larger linearly (solid line) or in stages (broken line) as the number of the power receiving vehicles becomes greater.

Next, at step S106, the power transmission control part 63 decreases the power transmitted from the power transmission apparatus 4 to the power reception apparatus 5 in accordance with the amount of decrease in the transmitted power determined at step S105. For example, the power transmission control part 63 decreases the transmitted power by decreasing the voltage value of the alternating current voltage supplied from the inverter 42 to the power transmission side resonance circuit 43 from the initial value.

On the other hand, if at step S103 it is judged that there has been no pickup/dropoff operation, the present control routine proceeds to step S107. At step S107, the power transmission control part 63 initializes the value of the power transmitted from the power transmission apparatus 4 to the power reception apparatus 5. For example, the power transmission control part 63 sets the voltage value of the alternating current voltage supplied from the inverter 42 to the power transmission side resonance circuit 43 to the initial value.

After step S106 or step S107, the present control routine proceeds to step S108. At step S108, the power transmission control part 63 judges whether a predetermined power supply end condition stands. The power supply end condition is, for example, a predetermined time period elapsing from when power transmission from the power transmission apparatus 4 to the power reception apparatus 5 was started, it being judged that the vehicle 3 passes over the power transmission side resonance circuit 43 of the power transmission apparatus 4, or the vehicle 3 stopping transmitting the power supply request signal.

If at step S108 it is judged that a power supply end condition does not stand, the present control routine returns to step S103 and it is again judged that there is any pickup/dropoff operation. On the other hand, if it is judged that a power supply end condition stands, the present control routine proceeds to step S109.

At step S109, the power transmission control part 63 stops the transmission of power from the power transmission apparatus 4 to the power reception apparatus 5. Specifically, the power transmission control part 63 stops the supply of power from the inverter 42 to the power transmission side resonance circuit 43. After step S109, the present control routine ends.

Second Embodiment

The configuration and control of the power supply apparatus according to a second embodiment are basically similar to the configuration and control of the power supply apparatus according to the first embodiment except for the points explained below. For this reason, below, the second embodiment of the present disclosure will be explained focusing on parts different from the first embodiment.

If there is a pickup/dropoff operation at a vehicle 3 being supplied with power, the passenger being picked up or dropped off may be wearing a pacemaker. In this case, it is desirable to avoid as much as possible exposure of the passenger to electromagnetic waves. For this reason, in the second embodiment, if a pickup/dropoff operation at the vehicle 3 is detected, the power transmission control part 63 stops the transmission of power from the power transmission apparatus 4 to the power reception apparatus 5 if the passenger being picked up or dropped off is wearing a pacemaker. By doing this, it is possible to increase much more the safety when the power supply apparatus 2 supplies power by non-contact to the vehicle 3.

Figure 7:
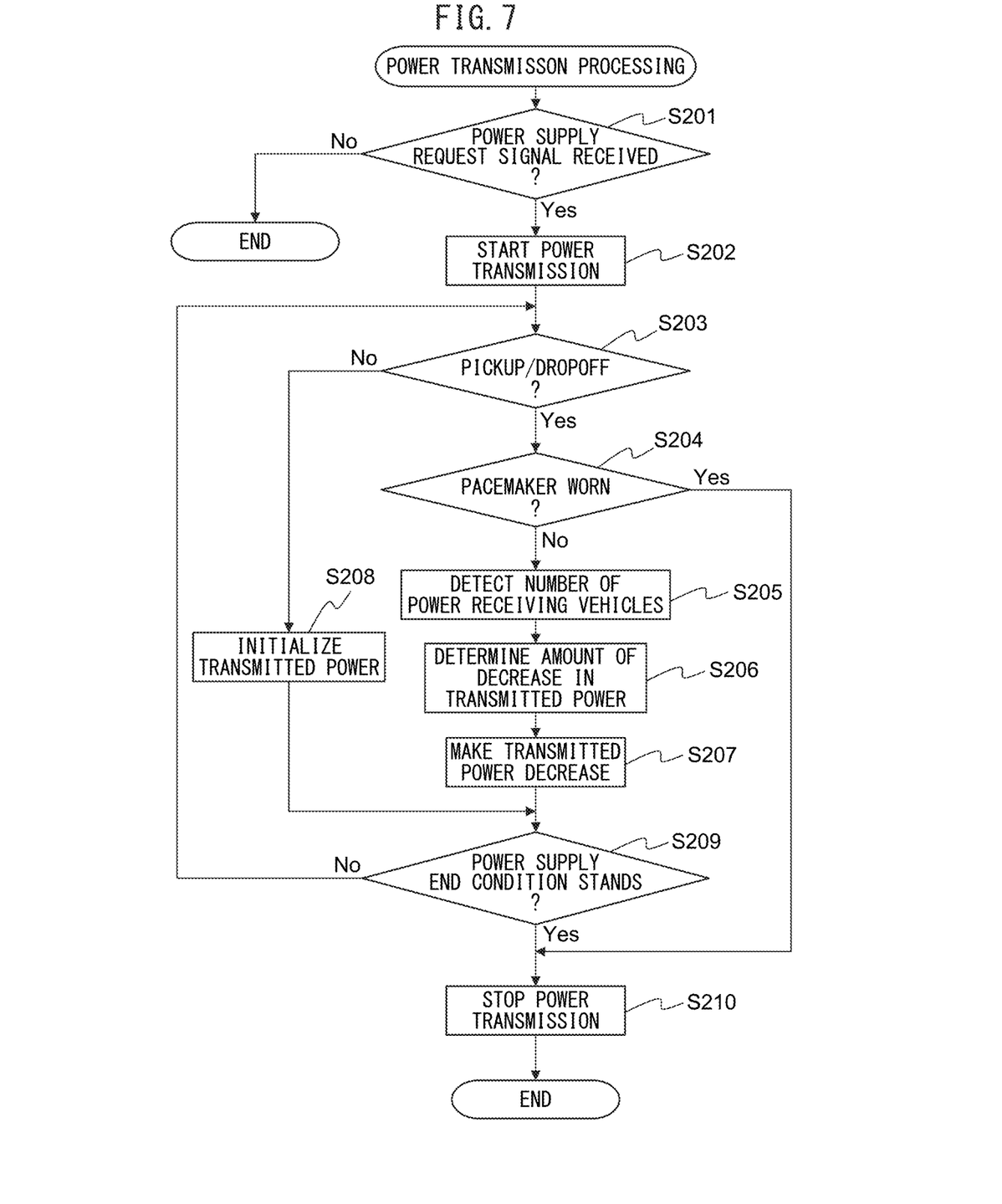
FIG. 7 is a flow chart showing a control routine of power transmission processing in a second embodiment of the present disclosure.

FIG. 7 is a flow chart showing a control routine of power transmission processing in the second embodiment of the present disclosure. The present control routine is repeatedly performed by the controller 6 of the power supply apparatus 2.

Steps S201 to S203 are performed in the same way as steps S101 to S103 of FIG. 5. If at step S203 it is judged that there is a pickup/dropoff operation at the vehicle 3, the present control routine proceeds to step S204.

At step S204, the pickup/dropoff detection part 64 judges whether the passenger being picked up or dropped off is wearing a pacemaker. For example, passenger information including any wearing of a pacemaker is transmitted together with the power supply request signal from the vehicle 3. The pickup/dropoff detection part 64 judges whether the passenger being picked up or dropped off is wearing a pacemaker based on the passenger information. The passenger information includes not only information on passengers in the vehicle 3, but also information on passengers scheduled to be picked up by the vehicle 3. For example, if the vehicle 3 is owned by a user, the user inputs passenger information in advance to an input device of the vehicle 3 (for example, HMI) etc. On the other hand, if the vehicle 3 is a taxi or other such vehicle providing a passenger transport service, when a user reserves a pickup by the vehicle 3, passenger information input by the user is transmitted from the user terminal to the vehicle 3.

If at step S204 it is judged that a passenger being picked up or dropped off is wearing a pacemaker, the present control routine proceeds to step S210. At step S210, in the same way as step S109 of FIG. 5, the power transmission control part 63 stops the transmission of power from the power transmission apparatus 4 to the power reception apparatus 5. After step S210, the present control routine ends. On the other hand, if at step S204 it is judged that a passenger being picked up or dropped off is not wearing a pacemaker, steps S205 to S207 and S209 are performed in the same way as steps S104 to S106 and S108 of FIG. 5.

Third Embodiment

The configuration and control of the power supply apparatus according to a third embodiment are basically similar to the configuration and control of the power supply apparatus according to the first embodiment except for the points explained below. For this reason, below, the third embodiment of the present disclosure will be explained focusing on parts different from the first embodiment.

If there is a pickup/dropoff operation at a vehicle 3 being supplied with power, the greater the number of passengers performing the pickup/dropoff operation, the greater the degree of effect of electromagnetic waves on the electronic equipment of the passengers etc. For this reason, in the third embodiment, in addition to the number of the power receiving vehicles, the number of passengers being picked up or dropped off is also considered in determining the amount of power decrease of power transmitted from the power transmission apparatus 4 to the power reception apparatus 5.

Specifically, the pickup/dropoff detection part 64 identifies the number of passengers being picked up or dropped off at the vehicle 3. Based on the number of the power receiving vehicles detected by the power receiving vehicle detection part 65 and the number of passengers identified by the pickup/dropoff detection part 64, the power transmission control part 63 determines the amount of decrease of power transmitted from the power transmission apparatus 4 to the power reception apparatus 5. By doing this, it is possible to set the power transmitted from the power transmission apparatus 4 to the power reception apparatus 5 when passengers of the vehicle 3 are being picked up or dropped off to a more suitable value.

Figure 8:
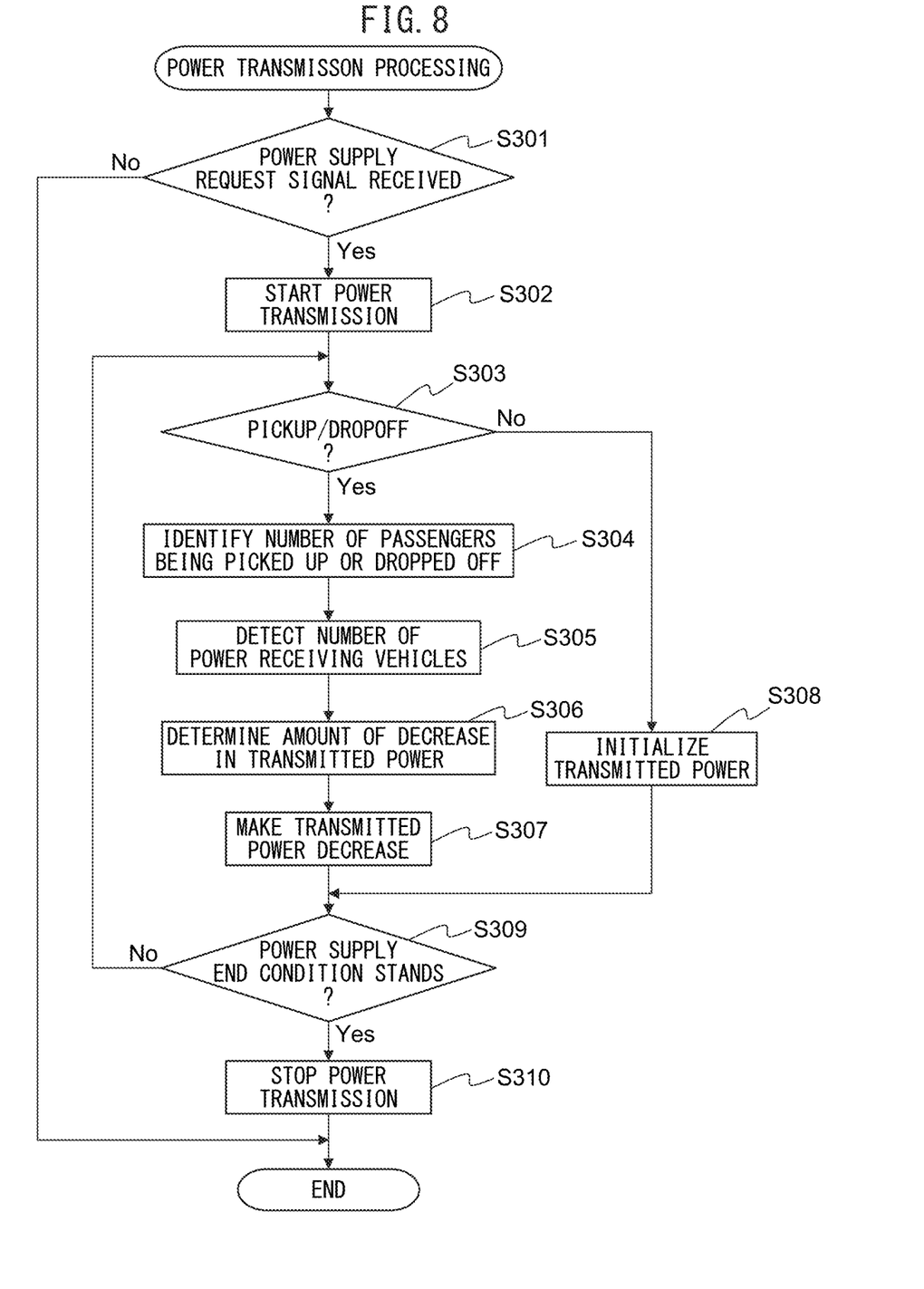
FIG. 8 is a flow chart showing a control routine of power transmission processing in a third embodiment of the present disclosure.

FIG. 8 is a flow chart showing a control routine of power transmission processing in the third embodiment of the present disclosure. The present control routine is repeatedly performed by the controller 6 of the power supply apparatus 2.

Steps S301 to S303 are performed in the same way as steps S101 to S103 of FIG. 5. If at step S303 it is judged that there is a pickup/dropoff operation at the vehicle 3, the present control routine proceeds to step S304.

At step S304, the pickup/dropoff detection part 64 identifies the number of passengers being picked up or dropped off at the vehicle 3. For example, the pickup/dropoff detection part 64 identifies the number of passengers being picked up or dropped off at the vehicle 3 based on an image generated by a camera provided at the power supply apparatus 2.

Further, passenger information including the number of persons being picked up or the number of persons scheduled to be picked up may be transmitted from the vehicle 3 along with a power supply request signal, and the pickup/dropoff detection part 64 may identify the number of passengers being picked up or dropped off based on the passenger information. The number of persons being picked up is, for example, acquired by the ECU 7 of the vehicle 3 based on the output of an internal vehicle camera, seat belt sensors, seat occupancy sensors, a weight sensor, etc. Further, if the vehicle 3 is a vehicle like a taxi providing a passenger transport service, the number of persons scheduled to be picked up input by a user when a user reserves pickup by a vehicle 3 is transmitted from the user terminal to the vehicle 3.

Next, at step S305, in the same way as step S104 of FIG. 5, the power receiving vehicle detection part 65 detects the number of the power receiving vehicles.

Figure 9:
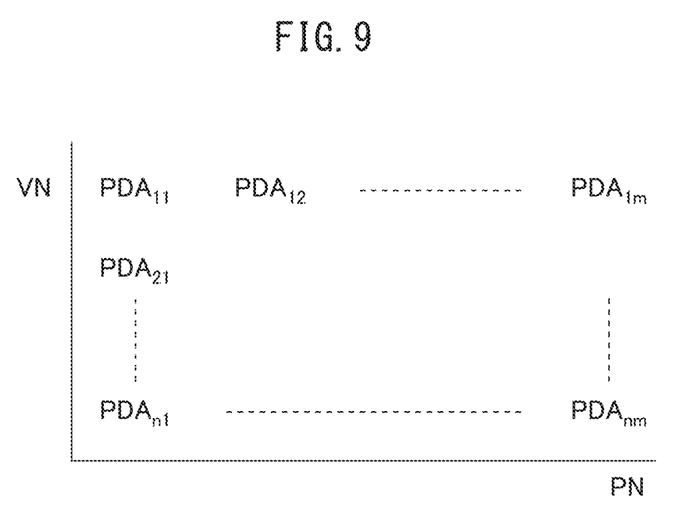
FIG. 9 is a view showing a map for determining an amount of decrease in transmitted power based on a number of passengers being picked up or dropped off and a number of power receiving vehicles.

Next, at step S306, the power transmission control part 63 determines the amount of decrease of the power transmitted from the power transmission apparatus 4 to the power reception apparatus 5 based on the number of passengers identified by the pickup/dropoff detection part 64 and the number of power receiving vehicles detected by the power receiving vehicle detection part 65. For example, the power transmission control part 63 uses a two-dimensional map such as shown in FIG. 9 to determine the amount of decrease PDA of the transmitted power based on the number of passengers PN being picked up or dropped off and the number of the power receiving vehicles VN. This map is prepared in advance so that the greater the number of passengers PN, the larger the amount of decrease PDA becomes and the greater the number of the power receiving vehicles VN, the larger the amount of decrease PDA becomes.

Next, at step S307, in the same way as step S106 of FIG. 5, the power transmission control part 63 decreases the power transmitted from the power transmission apparatus 4 to the power reception apparatus 5 according to the amount of decrease of transmitted power determined at step S306. Next, the steps from step S309 are executed in the same way as step S108 of FIG. 5.

OTHER EMBODIMENTS

Above, preferred embodiments according to the present disclosure were explained, but the present disclosure is not limited to these embodiments and can be corrected and changed within the language of the claims.

For example, the vehicle 3 supplied with power by the power supply apparatus 2 may be a hybrid vehicle (HEV) or plug-in hybrid vehicle (PHEV) provided with an internal combustion engine and a motor as power sources for driving. Further, the vehicle 3 may be an automated driving vehicle in which at least a part of the acceleration, steering, and deceleration (braking) of the vehicle 3 is automatically controlled. Further, the vehicle 3 may be a commercial vehicle such as a bus or truck, an automated guide vehicle (AGV), etc.

Further, the method of noncontact power supply from the power supply apparatus 2 to the vehicle 3 is not limited to an electromagnetic induction system such as magnetic field resonance coupling. Various methods such as using an electrical field coupling system transmitting power using an electrical field as a medium can be used.

Further, the above-mentioned embodiments may be worked combined in any way. For example, instead of steps S205 to S207 of FIG. 7, steps S304 to S307 of FIG. 8 may be performed.

REFERENCE SIGNS LIST 2. power supply apparatus
3. vehicle
4. power transmission apparatus
5. power reception apparatus
6. controller
62. processor
63. power transmission control part
64. pickup/dropoff detection part
65. power receiving vehicle detection part

The invention claimed is:

1. A power supply apparatus for supplying power to a vehicle by non-contact, comprising:
  a power transmission apparatus configured to transmit power to a power reception apparatus of the vehicle by non-contact; and
  a processor configured to
    control the power transmission apparatus,
    while the power is being supplied by non-contact from the power supply apparatus to the vehicle, detect a pickup/dropoff operation at the vehicle based on a result of detection of the pickup/dropoff operation transmitted from the vehicle to the power supply apparatus, and
    detect a number of surrounding vehicles being supplied with power by non-contact in a predetermined range at surroundings of the power supply apparatus,
  wherein the processor is configured to, in response to the pickup/dropoff operation being detected,
    determine, based on the number of surrounding vehicles, an amount of decrease of the power transmitted from the power transmission apparatus to the power reception apparatus, and
    decrease the power transmitted from the power transmission apparatus to the power reception apparatus by the determined amount.

2. The power supply apparatus according to claim 1, wherein
  the processor is configured to, in response to a passenger being picked up or dropped off wearing a pacemaker while the pickup/dropoff operation is detected, stop power transmission from the power transmission apparatus to the power reception apparatus.

3. The power supply apparatus according to claim 1, wherein
  the processor is configured to
    identify a number of passengers being picked up or dropped off in the pickup/dropoff operation, and
    determine the amount of decrease of the transmitted power based on the number of surrounding vehicles and the number of passengers.

4. A power supply method, comprising:
- transmitting power from a power transmission apparatus of a power supply apparatus to a power reception apparatus of a vehicle by non-contact to supply power from the power supply apparatus to the vehicle by non-contact;
- while the power is being supplied by non-contact from the power supply apparatus to the vehicle, detecting a pickup/dropoff operation at the vehicle based on a result of detection of the pickup/dropoff operation transmitted from the vehicle to the power supply apparatus;
- detecting a number of surrounding vehicles being supplied with power by non-contact in a predetermined range at the surroundings of the power supply apparatus; and
- in response to the pickup/dropoff operation being detected,
  - determining, based on the number of surrounding vehicles, an amount of decrease of the power transmitted from the power transmission apparatus to the power reception apparatus, and
  - decreasing the power transmitted from the power transmission apparatus to the power reception apparatus by the determined amount.

5. The power supply apparatus according to claim 1, wherein
the detection of the pickup/dropoff operation is determined based on the result of detection of a door of the vehicle being opened.

6. The power supply apparatus according to claim 1, wherein
the detection of the pickup/dropoff operation is determined based on the result of detection from
- an internal vehicle camera generating an image of an inside of a passenger compartment of the vehicle,
- one or more seat belt sensors detecting fastening of corresponding one or more seatbelts of the vehicle,
- one or more seating sensors detecting seating of one or more passengers in the vehicle, or
- a weight sensor detecting a weight of the vehicle.

7. The power supply apparatus according to claim 1, further comprising:
a camera configured to generate an image; wherein
the processor is configured to
- identify, based on the image from the camera, a number of passengers being picked up or dropped off in the pickup/dropoff operation, and
- determine the amount of decrease of the transmitted power based on the number of surrounding vehicles and the number of passengers.

8. The power supply method according to claim 4, further comprising:
in response to a passenger being picked up or dropped off wearing a pacemaker while the pickup/dropoff operation is detected, stopping power transmission from the power transmission apparatus to the power reception apparatus.

9. The power supply method according to claim 4, further comprising:
- identifying, based on an image from a camera of the power supply apparatus, a number of passengers being picked up or dropped off in the pickup/dropoff operation, and
- determining the amount of decrease of the transmitted power based on the number of surrounding vehicles and the number of passengers.

10. The power supply method according to claim 4, wherein
in said detecting of the pickup/dropoff operation at the vehicle, the detection of the pickup/dropoff operation is determined based on the result of detection of a door of the vehicle being opened.

11. The power supply method according to claim 4, wherein
in said detecting of the pickup/dropoff operation at the vehicle, the detection of the pickup/dropoff operation is determined based on the result of detection from
- an internal vehicle camera generating an image of an inside of a passenger compartment of the vehicle,
- one or more seat belt sensors detecting fastening of corresponding one or more seatbelts of the vehicle,
- one or more seating sensors detecting seating of one or more passengers in the vehicle, or
- a weight sensor detecting a weight of the vehicle.

* * * * *